United States Patent
Ito et al.

(10) Patent No.: US 10,774,025 B2
(45) Date of Patent: Sep. 15, 2020

(54) METHOD FOR PRODUCING POLYFUNCTIONAL ACRYLATE

(71) Applicant: OSAKA ORGANIC CHEMICAL INDUSTRY LTD., Osaka (JP)

(72) Inventors: Keisuke Ito, Hakusan (JP); Shigeaki Matsumoto, Hakusan (JP); Keita Shigematsu, Hakusan (JP)

(73) Assignee: OSAKA ORGANIC CHEMICAL INDUSTRY LTD., Osaka (JP)

( * ) Notice: Subject to any disclaimer, the term of this patent is extended or adjusted under 35 U.S.C. 154(b) by 0 days.

(21) Appl. No.: 16/607,018

(22) PCT Filed: Apr. 26, 2018

(86) PCT No.: PCT/JP2018/016906
§ 371 (c)(1),
(2) Date: Oct. 21, 2019

(87) PCT Pub. No.: WO2018/199203
PCT Pub. Date: Nov. 1, 2018

(65) Prior Publication Data
US 2020/0048178 A1    Feb. 13, 2020

(30) Foreign Application Priority Data
Apr. 26, 2017    (JP) ................. 2017-087637

(51) Int. Cl.
*C07C 67/03*    (2006.01)
*C07C 67/54*    (2006.01)
*C07C 69/54*    (2006.01)

(52) U.S. Cl.
CPC .............. *C07C 67/03* (2013.01); *C07C 67/54* (2013.01); *C07C 69/54* (2013.01)

(58) Field of Classification Search
CPC ......... C07C 67/03; C07C 67/54; C07C 69/54; C07B 61/00
See application file for complete search history.

(56) References Cited

U.S. PATENT DOCUMENTS 5,498,751 A * 3/1996 Trapasso ................. C07C 67/03
560/217

FOREIGN PATENT DOCUMENTS

| JP | H01-316389 A | 12/1989 |
|---|---|---|
| JP | 2003-261509 A | 9/2003 |
| JP | 2004-210685 A | 7/2004 |

OTHER PUBLICATIONS

Considine et al, Canadian Journal of Chemistry, Organotin Chemistry II. The Reaction of Diorganotin Oxides with Phenols, 1963, 41, pp. 1239-1243. (Year: 1963).*
Japanese Patent Office, International Search Report in International Patent Application No. PCT/JP2018/016906 (dated Aug. 7, 2018).

* cited by examiner

*Primary Examiner* — Paul A Zucker
(74) *Attorney, Agent, or Firm* — Leydig, Voit & Mayer, Ltd.

(57) ABSTRACT

The present invention provides a production method of a multifunctional acrylate with a reduced tin content which includes adding an acid to a mixture containing an organotin compound and a multifunctional acrylate and distilling the mixture containing the acid.

20 Claims, No Drawings

METHOD FOR PRODUCING POLYFUNCTIONAL ACRYLATE

CROSS-REFERENCE TO RELATED APPLICATIONS

This patent application is the U.S. national phase of International Patent Application No. PCT/JP2018/016906, filed Apr. 26, 2018, which claims the benefit of Japanese Patent Application No. 2017-087637, filed on Apr. 26, 2017, which are incorporated by reference in their entireties herein.

TECHNICAL FIELD

The present invention relates to a production method of a multifunctional acrylate.

BACKGROUND ART

Acrylate (i.e., acrylic ester) is useful as a material or the like of a polymer. As a production method of the acrylate, a transesterification reaction using an organotin compound as a catalyst is known. To reduce the content of tin in the acrylate which is a resultant product of the transesterification reaction, various methods such as distillation and the like have heretofore been performed. For example, patent document 1 describes that a transesterification reaction of (meth)acrylate and alcohol as the materials produces a reaction solution containing (meth)acrylate which is the resultant product, then the (meth)acrylate as the material is separated from the reaction solution and an ion-exchange resin is contacted with the rest of the reaction solution.

DOCUMENT LIST

Patent Document patent document 1: JP-A-2003-261509

SUMMARY OF THE INVENTION

Problems to be Solved by the Invention

A multifunctional acrylate (i.e., acrylic ester having two or more acryloyl groups in one molecule) obtained from acrylate and polyhydric alcohol by a transesterification reaction using an organotin compound as a catalyst has a higher boiling point compared with a monofunctional acrylate (i.e., acrylic ester having one acryloyl group in one molecule) obtained from acrylate and monohydric alcohol. When a multifunctional acrylate is obtained by distillation from a mixture containing an organotin compound and a multifunctional acrylate obtained after a transesterification reaction, an organotin compound is mixed in a distillate (purified multifunctional acrylate) and the tin content cannot be sufficiently reduced. The present invention has been made taking note of such situation and aims to obtain a multifunctional acrylate with a reduced tin content.

Means of Solving the Problems

The present inventors have conducted intensive studies and found that a multifunctional acrylate with a reduced tin content can be obtained by adding an acid to a mixture containing an organotin compound and a multifunctional acrylate and distilling the mixture containing the acid. The present invention based on this finding is as follows.

[1] A method for producing a multifunctional acrylate with a reduced tin content comprising adding an acid to a mixture comprising an organotin compound and a multifunctional acrylate and distilling the mixture comprising the acid.

[2] The production method of the aforementioned [1] wherein an amount of the acid to be added is 50-500 parts by weight per 100 parts by weight of a content of tin in the mixture comprising the organotin compound and the multifunctional acrylate.

[3] A method for producing a multifunctional acrylate comprising step 1 comprising a transesterification reaction of an acrylate and a polyhydric alcohol in the presence of an organotin compound to give a reaction mixture comprising the organotin compound and a multifunctional acrylate, step 2 comprising evaporating a compound having a boiling point lower than the organotin compound and the multifunctional acrylate from the reaction mixture to give a residue comprising the organotin compound and the multifunctional acrylate, step 3 comprising distilling the residue to give a distillate comprising the organotin compound and the multifunctional acrylate and a distillation residue comprising the organotin compound, and step 4 comprising adding an acid to the distillate and distilling the mixture comprising the acid to give a multifunctional acrylate with a reduced tin content.

[4] The production method of the aforementioned [3] wherein an amount of the acid to be added is 50-500 parts by weight per 100 parts by weight of a content of tin in the distillate comprising the organotin compound and the multifunctional acrylate.

[5] The production method of the aforementioned [3] or [4] wherein the distillation residue obtained in step 3 is reused in a transesterification reaction in a new step 1.

[6] The production method of any one of the aforementioned [3] to [5] wherein the polyhydric alcohol is a dihydric alcohol.

[7] The production method of the aforementioned [6] wherein the dihydric alcohol is a $C_{2-10}$ alkanediol.

[8] The production method of any one of the aforementioned [1] to [7] wherein the multifunctional acrylate is a difunctional acrylate.

[9] The production method of any one of the aforementioned [1] to [8] wherein the acid is an inorganic acid.

[10] The production method of any one of the aforementioned [1] to [9] wherein the organotin compound is a dialkyltin oxide.

[11] The production method of the aforementioned [10] wherein the dialkyltin oxide has two alkyl groups independently having a carbon number of 3-18.

Effect of the Invention

According to the production method of the present invention, a multifunctional acrylate with a reduced tin content can be obtained.

DESCRIPTION OF EMBODIMENTS

The production method of the present invention includes adding an acid to a mixture containing an organotin compound and a multifunctional acrylate and then distilling the mixture containing the acid. Only one kind or two or more kinds of acids may be used. The acid may be any of an inorganic acid and an organic acid, preferably an inorganic acid.

Examples of the inorganic acid include phosphoric acid, boric acid, hydrochloric acid (aqueous solution of hydrogen chloride), nitric acid, sulfuric acid and the like. Among the inorganic acids, phosphoric acid is more preferable. Examples of the organic acid include formic acid, acetic acid, propionic acid, butyric acid, valeric acid, hexanoic acid, heptanoic acid, octanoic acid, citric acid, malic acid, oxalic acid, malonic acid, succinic acid, glutaric acid, adipic acid, benzoic acid, phthalic acid, maleic acid, trimellitic acid, lauryl acid, citric acid and the like. Among the organic acids, malic acid, oxalic acid and maleic acid are preferable. Only one kind or two or more kinds of the inorganic acid and the organic acid may be used. In addition, an inorganic acid and an organic acid may be used in combination. Furthermore, an acid in the form of a hydrate (e.g., oxalic acid dihydrate) may be used. The acid may also be added as an aqueous solution.

The amount of the acid to be added is preferably 50-500 parts by weight, more preferably 50-200 parts by weight, further preferably 80-180 parts by weight, per 100 parts by weight of a content of tin in the mixture containing the organotin compound and the multifunctional acrylate. The content of tin does not refer to the content of the organotin compound but the content of Sn. As described in the below-mentioned mentioned Examples, the content of tin can be measured by high-frequency inductively-coupled plasma (ICP) emission spectrometry or inductively-coupled plasma mass spectrometry (ICP-MS).

Examples of the organotin compound include dialkyltin oxide and the like. Only one kind or two or more kinds of the dialkyltin oxide may be used.

The carbon number of the two alkyl groups of dialkyltin oxide is each independently preferably 3-18, more preferably 4-8. Examples of the dialkyltin oxide include dibutyltin oxide, dioctyltin oxide and the like. Among these, dioctyltin oxide is preferable.

The multifunctional acrylate is preferably a difunctional acrylate (i.e., acrylic ester having two acryloyl groups in one molecule), more preferably a difunctional acrylate represented by the formula (I):

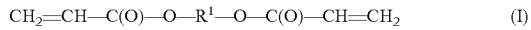

$$CH_2=CH-C(O)-O-R^1-O-C(O)-CH=CH_2 \quad (I)$$

wherein $R^1$ is a $C_{2-10}$ alkanediyl group. In the present invention, "$C_{x-y}$" means that the carbon number is not less than x and not more than y.

The alkanediyl group may be any of linear and branched chains. Examples of the $C_{2-10}$ alkanediyl group include ethane-1,2-diyl, propane-1,2-diyl, propane-1,3-diyl, butane-1,2-diyl, butane-1,3-diyl, butane-1,4-diyl, pentane-1,2-diyl, pentane-1,3-diyl, pentane-1,4-diyl, pentane-1,5-diyl, hexane-1,2-diyl, hexane-1,3-diyl, hexane-1,4-diyl, hexane-1,5-diyl, hexane-1,6-diyl, heptane-1,2-diyl, heptane-1,3-diyl, heptane-1,4-diyl, heptane-1,5-diyl, heptane-1,6-diyl, heptane-1,7-diyl, octane-1,2-diyl, octane-1,3-diyl, octane-1,4-diyl, octane-1,5-diyl, octane-1,6-diyl, octane-1,7-diyl, octane-1,8-diyl, nonane-1,9-diyl, decane-1,2-diyl, decane-1,10-diyl and the like. $R^1$ is preferably a $C_{3-9}$ alkanediyl group.

The mixture containing an acid may be distilled by batch distillation such as simple distillation or the like, or continuous distillation such as thin film distillation or the like.

When batch distillation is performed, the temperature thereof is preferably 40-200° C., more preferably 40-150° C., further preferably 60-130° C., and the pressure thereof is preferably 0.01-200 hPa, more preferably 0.01-100 hPa, further preferably 0.1-50 hPa.

When continuous distillation is performed, the temperature thereof preferably 40-160° C., more preferably 40-150° C., further preferably 60-120° C., and the pressure thereof is preferably 0.01-150 hPa, more preferably 0.01-100 hPa, further preferably 0.1-40 hPa.

In the present invention, the mixture containing the organotin compound and the multifunctional acrylate, which is the target of acid addition, is preferably a distillation residue obtained by the following steps 1 to 3. That is, a preferable embodiment of the production method of the present invention includes the following steps 1 to 4:

step 1 containing a transesterification reaction of an acrylate and a polyhydric alcohol in the presence of an organotin compound to give a reaction mixture containing the organotin compound and a multifunctional acrylate, step 2 containing evaporating a compound having a boiling point lower than the organotin compound and the multifunctional acrylate from the reaction mixture to give a residue containing the organotin compound and the multifunctional acrylate, step 3 containing distilling the residue to give a distillate containing the organotin compound and the multifunctional acrylate and a distillation residue containing the organotin compound, and step 4 containing adding an acid to the distillate and distilling the mixture containing the acid to give a multifunctional acrylate with a reduced tin content.

Steps 1 to 4 are described in this order in the following.
<Step 1>

In step 1, the transesterification reaction of an acrylate and a polyhydric alcohol is performed in the presence of an organotin compound. The organotin compound to be used in step 1 is as described above. The amount of the organotin compound to be used is preferably 0.1-10 parts by weight, more preferably 0.5-5 parts by weight, further preferably 0.5-2 parts by weight, per 100 parts by weight of the acrylate.

Examples of the acrylate include methyl acrylate, ethyl acrylate, n-propyl acrylate, isopropyl acrylate, n-butyl acrylate and the like. Only one kind or two or more kinds of the acrylate may be used and one kind of acrylate is preferably used. The acrylate is preferably methyl acrylate.

The amount of the acrylate to be used is preferably 0.5-10 mol, more preferably 0.8-5 mol, further preferably 1-3 mol, per 1 mol of the hydroxy group possessed by the polyhydric alcohol.

The polyhydric alcohol may be a dihydric alcohol having two hydroxy groups in one molecule or a polyhydric alcohol having not less than three hydroxy groups in one molecule. Only one kind or two or more kinds of the polyhydric alcohol may be used and one kind of polyhydric alcohol is preferably used.

The polyhydric alcohol is preferably a dihydric alcohol, more preferably a $C_{2-10}$ alkanediol. The $C_{2-10}$ alkanediol may be a linear or branched chain. Examples of the $C_{2-10}$ alkanediol include 1,2-ethanediol, 1,2-propanediol, 1,3-propanediol, 1,2-butanediol, 1,3-butanediol, 1,4-butanediol, 1,2-pentanediol, 1,3-pentanediol, 1,4-pentanediol, 1,5-pentanediol, 1,2-hexanediol, 1,3-hexanediol, 1,4-hexanediol, 1,5-hexanediol, 1,6-hexanediol, 1,2-heptanediol, 1,3-heptanediol, 1,4-heptanediol, 1,5-heptanediol, 1,6-heptanediol, 1,7-heptanediol, 1,2-octanediol, 1,3-octanediol, 1,4-octanediol, 1,5-octanediol, 1,6-octanediol, 1,7-octanediol, 1,8-octanediol, 1,9-nonanediol, 1,2-decanediol, 1,10-decanediol and the like. The $C_{2-10}$ alkanediol is preferably a $C_{3-9}$ alkanediol.

Examples of the polyhydric alcohol having not less than three hydroxy groups in one molecule include glycerol, diglycerol, trimethylolpropane, ditrimethylolpropane, pentaerythritol, dipentaerythritol, sorbitol and the like.

The transesterification reaction is generally performed in a solvent. Examples of the solvent include hydrocarbon solvents such as n-pentane, n-hexane, n-heptane, n-octane, 2,3-dimethylbutane, 2,5-dimethylhexane, 2,2,4-trimethylpentane, cyclohexane and the like, ether solvents such as cyclopentyl methyl ether and the like, ketone solvents such as methyl ethyl ketone, methyl isobutyl ketone and the like, and the like. Only one kind or two or more kinds of the solvents may be used. Among these, a hydrocarbon solvent is preferable, n-hexane and cyclohexane are more preferable, and cyclohexane is further preferable.

The transesterification reaction is preferably performed in the presence of a polymerization inhibitor to prevent polymerization of acrylate. Examples of the polymerization inhibitor include N-oxy radical compounds such as 4-hydroxy-2,2,6,6-tetramethylpiperidine-N-oxyl, 4-acetylamino-2,2,6,6-tetramethylpiperidine-N-oxyl (AMX), 4-benzoyloxy-2,2,6,6-tetramethylpiperidine-N-oxyl, 4-oxo-2,2,6,6-tetramethylpiperidine-N-oxyl, 2,2,6,6-tetramethylpiperidine-N-oxyl and the like; phenol compounds such as 4-methoxyphenol (MEHQ), 2,2'-methylenebis(4-ethyl-6-tert-butylphenol), 2,6-di-tert-butyl-4-methylphenol, 2,6-di-tert-butyl-N,N-dimethylamino-p-cresol, 2,4-dimethyl-6-tert-butylphenol, 4-tert-butylcatechol, 4,4'-thio-bis(3-methyl-6-tert-butylphenol), 4,4'-butylidene-bis(3-methyl-6-tert-butylphenol) and the like; quinone compounds such as methoquinone, hydroquinone, 2,5-di-tert-butylhydroquinone, 2,6-di-tert-butylhydroquinone, benzoquinone and the like; copper dialkyldithiocarbamates such as copper dimethyldithiocarbamate, copper diethyldithiocarbamate and the like; amino compounds such as phenothiazine, N,N'-diphenyl-β-phenylenediamine, phenyl-p-naphthylamine, N,N'-di-p-naphthyl-p-phenylenediamine, N-phenyl-N'-isopropyl-p-phenylenediamine and the like; hydroxyamine compounds such as 1,4-dihydroxy-2,2,6,6-tetramethylpiperidine, 1-hydroxy-2,2,6,6-tetramethylpiperidine, 4-hydroxy-2,2,6,6-tetramethylpiperidine and the like; ferric chloride, cuprous chloride and the like. Only one kind or two or more kinds of the polymerization inhibitors may be used. Among these, MEHQ and AMX are preferable. When a polymerization inhibitor is used, the amount thereof is preferably $1 \times 10^{-5}$-$1 \times 10^{-2}$ parts by weight, more preferably $5 \times 10^{-5}$-$3 \times 10^{-3}$ parts by weight, per 1 part by weight of the acrylate.

The temperature of the transesterification reaction is preferably 50-150° C., more preferably 60-100° C., and the pressure at that time is preferably 50 hPa—ordinary pressure, more preferably 100 hPa—ordinary pressure. The transesterification reaction is preferably performed while removing byproducts (e.g., methanol etc.) from the system. The ordinary pressure here means a pressure when a depressurization or pressurization operation is not performed and is almost the same as the atmospheric pressure.

<Step 2>

In step 2, a compound having a boiling point lower than the organotin compound and the multifunctional acrylate (hereinafter sometimes to be abbreviated as "low-boiling-point compound") is distillated from the reaction mixture obtained in step 1 to give a residue containing the organotin compound and the multifunctional acrylate.

The low-boiling-point compound is typically the remainder of the materials used in step 1 (acrylate and polyhydric alcohol), the solvent used in step 1, and byproducts (e.g., methanol) remaining in the reaction mixture.

The temperature of the evaporation of the low-boiling-point compound is preferably 20-100° C., more preferably 40-90° C., further preferably 40-70° C., and the pressure at that time is preferably 10 hPa—ordinary pressure, more preferably 30 hPa—ordinary pressure, further preferably 80 hPa—ordinary pressure.

<Step 3>

In step 3, the residue obtained in step 2 is distillated to give a distillate containing the organotin compound and the multifunctional acrylate and a distillation residue containing the organotin compound.

The distillation in step 3 may be batch distillation such as simple distillation or the like, or continuous distillation such as thin film distillation or the like. The distillation in step 3 is preferably continuous distillation, more preferably thin film distillation.

When batch distillation is performed in step 3, the temperature thereof is preferably 40-200° C., more preferably 40-150° C., further preferably 60-130° C., and the pressure thereof is, preferably 0.01-200 hPa, more preferably 0.01-100 hPa, further preferably 0.1-50 hPa.

When continuous distillation is performed in step 3, the temperature thereof is preferably 40-160° C., more preferably 40-150° C., further preferably 60-120° C., and the pressure thereof is preferably 0.01-150 hPa, more preferably 0.01-100 hPa, further preferably 0.1-40 hPa.

The distillation residue obtained in step 3 contains a large amount of an organotin compound. Since the organotin compound is expensive, it is preferable to reuse the distillation residue obtained in step 3 in a transesterification reaction in a new step 1.

<Step 4>

In step 4, an acid is added to the distillate obtained in step 3 and the mixture containing the acid is distilled to give a multifunctional acrylate with a reduced tin content. The acid, organotin compound and multifunctional acrylate are as described above.

The amount of the acid to be added is preferably 50-500 parts by weight, more preferably 50-200 parts by weight, further preferably 80-180 parts by weight, per 100 parts by weight of a content of tin in the distillate containing the organotin compound and the multifunctional acrylate.

The distillation in step 4 may be batch distillation such as simple distillation or the like, or continuous distillation such as thin film distillation or the like. The distillation in step 4 is preferably batch distillation, more preferably simple distillation.

When batch distillation is performed in step 4, the temperature thereof is preferably 40-200° C., more preferably 40-150° C., further preferably 60-130° C., and the pressure thereof is preferably 0.01-200 hPa, more preferably 0.01-100 hPa, further preferably 0.1-50 hPa.

When continuous distillation is performed in step 4, the temperature thereof is preferably 40-160° C., more preferably 40-150° C., further preferably 60-120° C., and the pressure thereof is, preferably 0.01-150 hPa, more preferably 0.01-100 hPa, further preferably 0.1-40 hPa.

EXAMPLE

The present invention is described in more detail in the following by referring to Examples. The present invention is not limited by the following examples, and appropriate modifications can of course be also added within the scope compatible with the gist described above and below, all of which are included in the technical scope of the present invention.

Example 1

(1) Transesterification Reaction (Step 1)

An oldershaw distillation column (20 plates), a reflux condenser and an air introducing tube were set on a 1 L glass four-neck flask, 1,3-butanediol (162.2 g, 1.8 mol), methyl acrylate (462.6 g, 5.4 mol), cyclohexane (122.2 g), and 4-methoxyphenol (MEHQ) (0.04 g) and 4-acetylamino-2,2,6,6-tetramethylpiperidine-N-oxyl (AMX) (0.07 g) as polymerization inhibitors were charged in the flask, dioctyltin oxide (6.50 g, 0.018 mol) was added, and 1,3-butanediol and methyl acrylate were reacted for 16 hr under the conditions of temperature 90° C. and ordinary pressure while removing the produced azeotropic mixture of methanol and cyclohexane.

The produced azeotropic mixture of methanol and cyclohexane was placed in a decanter, water (50 mL) was added into the decanter, and 1,3-butanediol and methyl acrylate were reacted while removing the separated aqueous layer (methanol aqueous solution) from the decanter until the distillation of methanol disappeared mostly. The organic layer (cyclohexane solution containing methyl acrylate) in the decanter was refluxed in the tenth plate of the oldershaw distillation column.

The reaction solution obtained after completion of the reaction between 1,3-butanediol and methyl acrylate was 620.3 g. The obtained reaction solution was analyzed by gas chromatography (GC) under the following conditions to find the composition thereof of 1,3-butanediol diacrylate 98.7 area % and 1,3-butanediol monoacrylate 1.3 area %.
Measurement Apparatus: gas chromatograph (GC) system 7890A manufactured by Agilent Technologies
Detector: FID (flame ionization detector)
Column: capillary column DB-1701 30m (manufactured by Agilent Technologies)
Carrier Gas: helium (2) Evaporation of Low-Boiling-Point Compound (Step 2)

The total amount of the reaction solution after the analysis and obtained in the above-mentioned (1) was charged in a 1 L three-neck flask, the temperature in the flask was adjusted to 68-85° C., and methyl acrylate and cyclohexane were evaporated at pressure 15-300 hPa to give a residue (363.4 g). The obtained residue was analyzed by gas chromatography under the above-mentioned conditions to find the composition thereof of 1,3-butanediol diacrylate 98.7 area % and 1,3-butanediol monoacrylate 1.6 area %.

(3) Distillation (Step 3)

The total amount of the residue after the analysis and obtained in the above-mentioned (2) was charged in a 500 mL dropping funnel, and distilled in a thin film distiller adjusted to an outercoat temperature of 100° C. and a degree of pressure reduction of 1 hPa or below to give a distillate (330.2 g). The obtained distillate was analyzed by gas chromatography under the above-mentioned conditions to find the composition thereof of 1,3-butanediol diacrylate 97.9 area % and 1,3-butanediol monoacrylate 1.8 area %. The obtained distillate was analyzed by high-frequency inductively-coupled plasma (ICP) emission spectrometry under the following conditions to find the content of tin of 36.4 ppm (weight basis).
Measurement Apparatus: SPS5100 type manufactured by SII NanoTechnology
Measurement Operation The distillate was measured in a quartz beaker, sulfuric acid and nitric acid were added and thermolysis was performed. After allowing to cool, ultrapure water was added to the mixture, and a give volume of a solution for measurement was prepared and used for high-frequency inductively-coupled plasma (ICP) emission spectrometry.

(4) Addition of Acid and Distillation (Step 4)

The distillate (330.0 g) obtained in the above-mentioned (3) and 8.5 wt % phosphoric acid aqueous solution (0.12 g, phosphoric acid: 0.010 g, amount of phosphoric acid to be added per 100 parts by weight of content of tin in the distillate: 85 parts by weight) were charged in a 1 L three-neck flask and simple distillation was performed for 2 hr under conditions of flask temperature 101-107° C. and pressure 2.0 hPa or less to give 326.1 g of a distillate and 2.9 g of a distillation residue. The distillate was analyzed by inductively-coupled plasma mass spectrometry (ICP-MS) under the following conditions to find the content of tin of 5.2 ppb (weight basis). Measurement apparatus: ElanDRC type II manufactured by PerkinElmer
Measurement Operation The distillate was measured in a quartz beaker, sulfuric acid and nitric acid were added and thermolysis was performed. After allowing to cool, ultrapure water was added to the mixture, and a give volume of a solution for measurement was prepared and used for inductively-coupled plasma mass spectrometry (ICP-MS).

(5) Transesterification Reaction Reusing Distillation Residue (New Step 1)

In the same manner as in the above-mentioned (1) except that the distillation residue (28.0 g) containing dialkyltin oxide and obtained in the above-mentioned (2) was used instead of dioctyltin oxide (6.50 g) and the reaction time was set to 19 hr, a transesterification reaction was performed.

The reaction solution obtained after completion of the reaction between 1,3-butanediol and methyl acrylate was 639.8 g. The obtained reaction solution was analyzed by gas chromatography (GC) under the same conditions as the above-mentioned (1) to find the composition thereof of 1,3-butanediol diacrylate 98.5 area % and 1,3-butanediol monoacrylate 1.5 area %.

Comparative Example 1

The distillate (330.0 g) obtained in the same manner as in Example 1(3) (step 3) was charged in a 1 L three-neck flask and simple distillation was performed for 2 hr under conditions of flask temperature 101-107° C. and pressure 2.0 hPa or less to give 326.0 g of a distillate and 2.8 g of a distillation residue. The distillate was analyzed by inductively-coupled plasma mass spectrometry (ICP-MS) under the above-mentioned conditions to find the content of tin of 91.9 ppb (weight basis).

As shown by the comparison of Example 1 and Comparative Example 1, a multifunctional acrylate with a reduced tin content can be obtained as a distillate by adding an acid to a distillate containing an organotin compound (dioctyltin oxide) and a multifunctional acrylate (1,3-butanediol diacrylate) and further distilling the mixture.

Examples 2-10

In the same manner as in Example 1 except that the acid shown in the following Table 1 was added in step 4 instead of the 8.5 wt % phosphoric acid aqueous solution, a transesterification reaction (step 1), evaporation of a low-boilingpoint compound (step 2), distillation (step 3) and addition of an acid and distillation (step 4) were performed to give a distillate (1,3-butanediol diacrylate with reduced tin content).

The amount of the acid to be added per 100 parts by weight of content of tin in the distillate, and the content of tin in the obtained distillate (purified multifunctional acrylate) in step 4 are shown in the following Table 1. The amount of acid described in Table 1 does not show an amount of an acid aqueous solution but acid itself even when an acid aqueous solution is used. The content of tin was measured by inductively-coupled plasma mass spectrometry (ICP-MS) in the same manner as in the above.

TABLE 1

|  | acid added in step 4 | amount of acid to be added (parts by weight) | content of tin (ppb) |
|---|---|---|---|
| Example 2 | 10 wt % citric acid aqueous solution | 156 | 6.3 |
| Example 3 | 10 wt % dl-malic acid aqueous solution | 123 | 6.2 |
| Example 4 | 5 wt % oxalic acid aqueous dihydrate solution | 115 | 7.5 |
| Example 5 | 5 wt % succinic acid aqueous solution | 106 | 11.3 |
| Example 6 | phthalic acid | 156 | 12.4 |
| Example 7 | 10 wt % maleic acid aqueous solution | 106 | 10.8 |
| Example 8 | trimellitic acid | 188 | 16.5 |
| Example 9 | lauryl acid | 188 | 23.5 |
| Example 10 | 3 wt % boric acid aqueous solution | 57 | 58.5 |

INDUSTRIAL APPLICABILITY

According to the production method of the present invention, a multifunctional acrylate with a reduced tin content can be obtained.

This application is based on a patent application No. 2017-087637 filed in Japan, the contents of which are incorporated in full herein.

The invention claimed is:

1. A method for producing a multifunctional acrylate with a reduced tin content comprising adding an acid to a mixture comprising a dialkyltin oxide and a multifunctional acrylate and distilling the mixture comprising the acid.

2. The production method according to claim 1 wherein the amount of the acid to be added is 50-500 parts by weight per 100 parts by weight of the content of tin in the mixture comprising the dialkyltin oxide and the multifunctional acrylate.

3. A method for producing a multifunctional acrylate comprising
   step 1 comprising a transesterification reaction of an acrylate and a polyhydric alcohol in the presence of a dialkyltin oxide to give a reaction mixture comprising the dialkyltin oxide and a multifunctional acrylate,
   step 2 comprising evaporating a compound having a boiling point lower than the dialkyltin oxide and the multifunctional acrylate from the reaction mixture to give a residue comprising the dialkyltin oxide and the multifunctional acrylate,
   step 3 comprising distilling the residue to give a distillate comprising the dialkyltin oxide and the multifunctional acrylate and a distillation residue comprising the dialkyltin oxide, and
   step 4 comprising adding an acid to the distillate and distilling the mixture comprising the acid to give a multifunctional acrylate with a reduced tin content.

4. The production method according to claim 3 wherein the amount of the acid to be added is 50-500 parts by weight per 100 parts by weight of the content of tin in the distillate comprising the dialkyltin oxide and the multifunctional acrylate.

5. The production method according to claim 3 wherein the distillation residue obtained in step 3 is reused in a transesterification reaction in a new step 1.

6. The production method according to claim 3 wherein the polyhydric alcohol is a dihydric alcohol.

7. The production method according to claim 6 wherein the dihydric alcohol is a $C_{2-10}$ alkanediol.

8. The production method according to claim 1 wherein the multifunctional acrylate is a difunctional acrylate.

9. The production method according to claim 1 wherein the acid is an inorganic acid.

10. The production method according to claim 1 wherein the dialkyltin oxide has two alkyl groups independently having a carbon number of 3-18.

11. The production method according to claim 4 wherein the distillation residue obtained in step 3 is reused in a transesterification reaction in a new step 1.

12. The production method according to claim 11 wherein the polyhydric alcohol is a dihydric alcohol.

13. The production method according to claim 12 wherein the dihydric alcohol is a $C_{2-10}$ alkanediol.

14. The production method according to claim 13 wherein the multifunctional acrylate is a difunctional acrylate.

15. The production method according to claim 14 wherein the acid is an inorganic acid.

16. The production method according to claim 15 wherein the dialkyltin oxide has two alkyl groups independently having a carbon number of 3-18.

17. The production method according to claim 3 wherein the multifunctional acrylate is a difunctional acrylate.

18. The production method according to claim 3 wherein the acid is an inorganic acid.

19. The production method according to claim 3 wherein the dialkyltin oxide has two alkyl groups independently having a carbon number of 3-18.

20. The production method according to claim 3 wherein the multifunctional acrylate is a difunctional acrylate, the acid is an inorganic acid, and the dialkyltin oxide has two alkyl groups independently having a carbon number of 3-18.

* * * * *